United States Patent [19]

Stansbury

[11] 4,218,778

[45] Aug. 26, 1980

[54] HIGHLY STRETCHABLE GLOVE AND FORM FOR MAKING SAME

[75] Inventor: Benjamin Stansbury, Beverly Hills, Calif.

[73] Assignee: American Hospital Supply Corporation, Evanston, Ill.

[21] Appl. No.: 960,420

[22] Filed: Nov. 13, 1978

Related U.S. Application Data

[62] Division of Ser. No. 846,911, Oct. 31, 1977.

[51] Int. Cl.$^2$ ............................................. A41D 19/00
[52] U.S. Cl. ............................................. 2/163; 2/168
[58] Field of Search .................. 2/168, 167, 169, 163, 2/161 R, 161 A, 159

[56] References Cited

U.S. PATENT DOCUMENTS 1,241,941  10/1917  Dowd ...................................... 2/168
3,283,338  11/1966  Landau ................................. 2/163 X
3,707,005  12/1972  Giambrowe ............................ 2/163

Primary Examiner—H. Hampton Hunter
Attorney, Agent, or Firm—Larry N. Barger

[57] ABSTRACT

A highly stretchable latex rubber glove for use by physicians during surgery and the like. This glove has fingers, each of which have generally parallel sides, and are ovaled from front to back at a mid joint area of the fingers, and are ovaled from side to side at a tip section in an area of the wearer's finger directly beneath an approximate midpoint of the wearer's fingernail. This finger structure provides added flexibility and tactile sensitivity at tip sections of the glove fingers during delicate manuevers, such as tying sutures, etc. The glove also has an exaggerated undercut thumb ball area to provide improved stretchability diagonally across the glove's palm.

3 Claims, 9 Drawing Figures

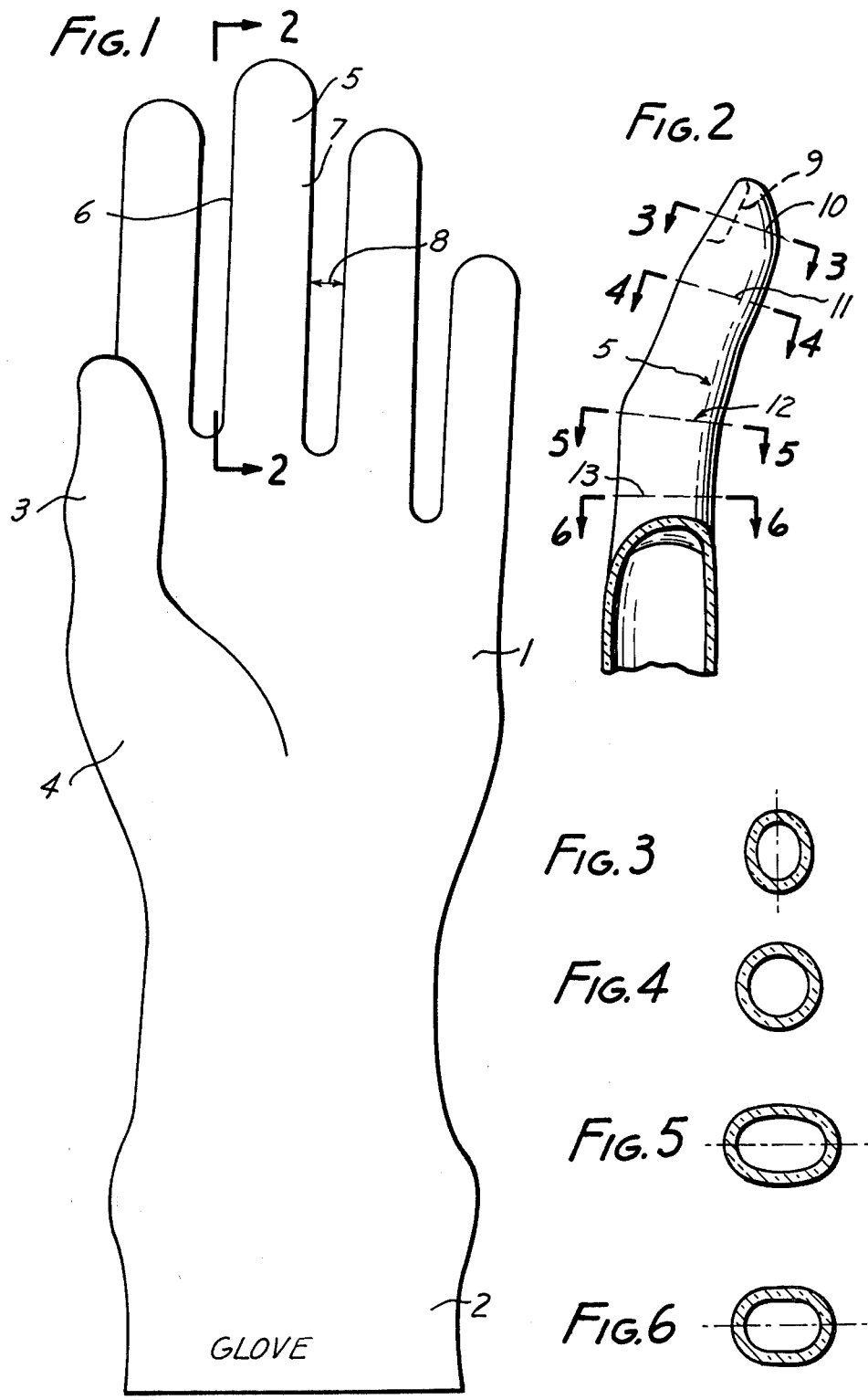

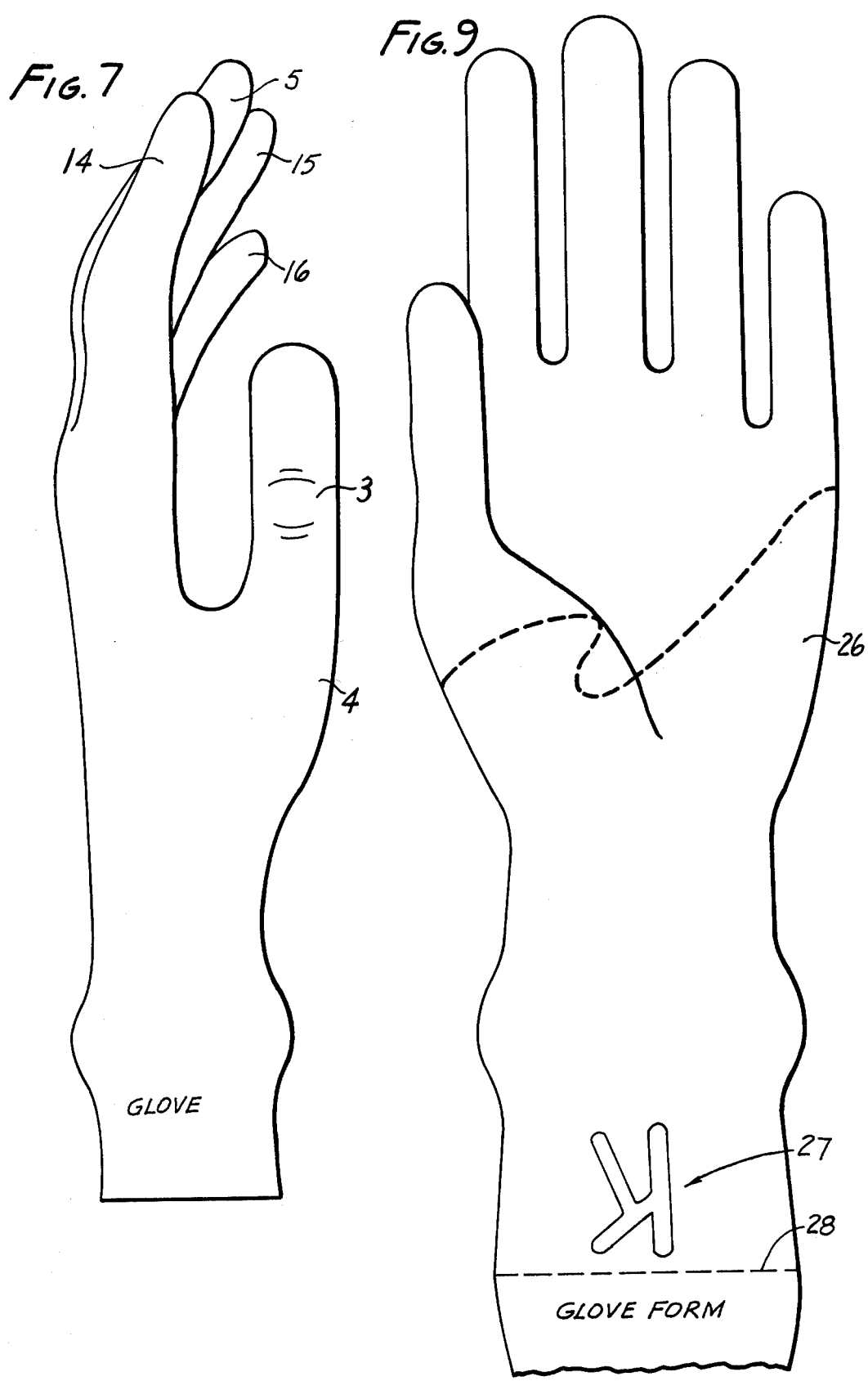

HIGHLY STRETCHABLE GLOVE AND FORM FOR MAKING SAME

This is a division of application Ser. No. 846,911, filed Oct. 31, 1977.

BACKGROUND OF THE INVENTION

Because of the many delicate manuevers, such as tying sutures, etc. performed by a surgeon, the fit and tactile sensitivity of a surgeon's latex glove is very critical. Particularly critical areas are the glove's palm, finger, and finger tip area. Since surgeon's gloves are sold sterile and disposed of after a single use, it is uneconomical to custom make the size and shape of the surgeon's glove to fit each individual surgeon. Thus, surgeon's glove sizes have developed over the years into 8-10 different sizes designed to fit the general population of surgeons. However, some surgeons find the glove fingers fitting too tightly or too loosely in the knuckle area, fingertip area, or palm area. In the past, several glove structures have been proposed to increase the comfort of fit to the wearer. These have included providing a glove finger that is generally ovaled in a front to rear direction along its length from its tip to its base while providing added material bumps in a first and second knuckle area of the fingers. This is described in the British Pat. No. 809,741. Another example of providing excess material in the knuckle area is in U.S. Pat. No. 1,097,018.

Other glove structures to improve fit comfort have included the provision of reduced diameters, cylindrical fingertip areas (U.S. Pat. No. 2,266,716), fingernail pockets (U.S. Pat. No. 2,056,555), and naturally bent fingers (U.S. Pat. No. 1,294,105). To improve the glove fit in the palm area, it has been proposed to gusset an external surface of the thumb ball area (U.S. Pat. No. 3,602,917), angularly dispose the thumb relative to the fingers (U.S. Pat. No. 3,613,172), and provide a bulged area at a rear wall of the glove palm section (U.S. Pat. No. 3,867,727).

SUMMARY OF THE INVENTION

This invention relates to an improved finger shape and thumb ball shape of the glove to improve comfort of fit and tactile sensitivity in a surgeon's glove. The fingers have a tip section corresponding to a midpoint in the wearer's fingernail that is ovaled from a side to side of the glove finger. The glove has a first knuckle section immediately behind the tip section and a second knuckle section corresponding to a midpoint along a wearer's finger. This second knuckle area of the glove finger is substantially ovaled in a direction from a front to back of the glove finger. Each finger of the glove has sides that are approximately parallel between the fingertip and base of the glove finger for ease of dip forming and removal from a glove form.

The glove also has an exaggerated thumb ball portion with an undercut section in the palm area to provide additional material for stretching diagonally across the thumb palm from a ball of the thumb to a base of the little finger portion of the glove. The glove's palm area along this diagonal direction requires a wide range of stretch without causing the palm to loosely buckle or form a loose baggy portion in the gloove palm as the surgeon flexes his thumb ball when manipulating his thumb in opposition to his various fingers.

THE DRAWINGS

FIG. 1 is a front elevational view of the glove;

FIG. 2 is a sectional view taken along line 2—2 of FIG. 1;

FIG. 3 is a sectional view taken along line 3—3 of FIG. 2;

FIG. 4 is a sectional view taken along line 4—4 of FIG. 2;

FIG. 5 is a sectional view taken along line 5—5 of FIG. 2;

FIG. 6 is a sectional view taken along line 6—6 of FIG. 2;

FIG. 7 is a side elevational view of the glove of FIG. 1;

FIG. 9 is a front elevational view of a form for making the glove of FIG. 1.

DETAILED DESCRIPTION

Figure 8:
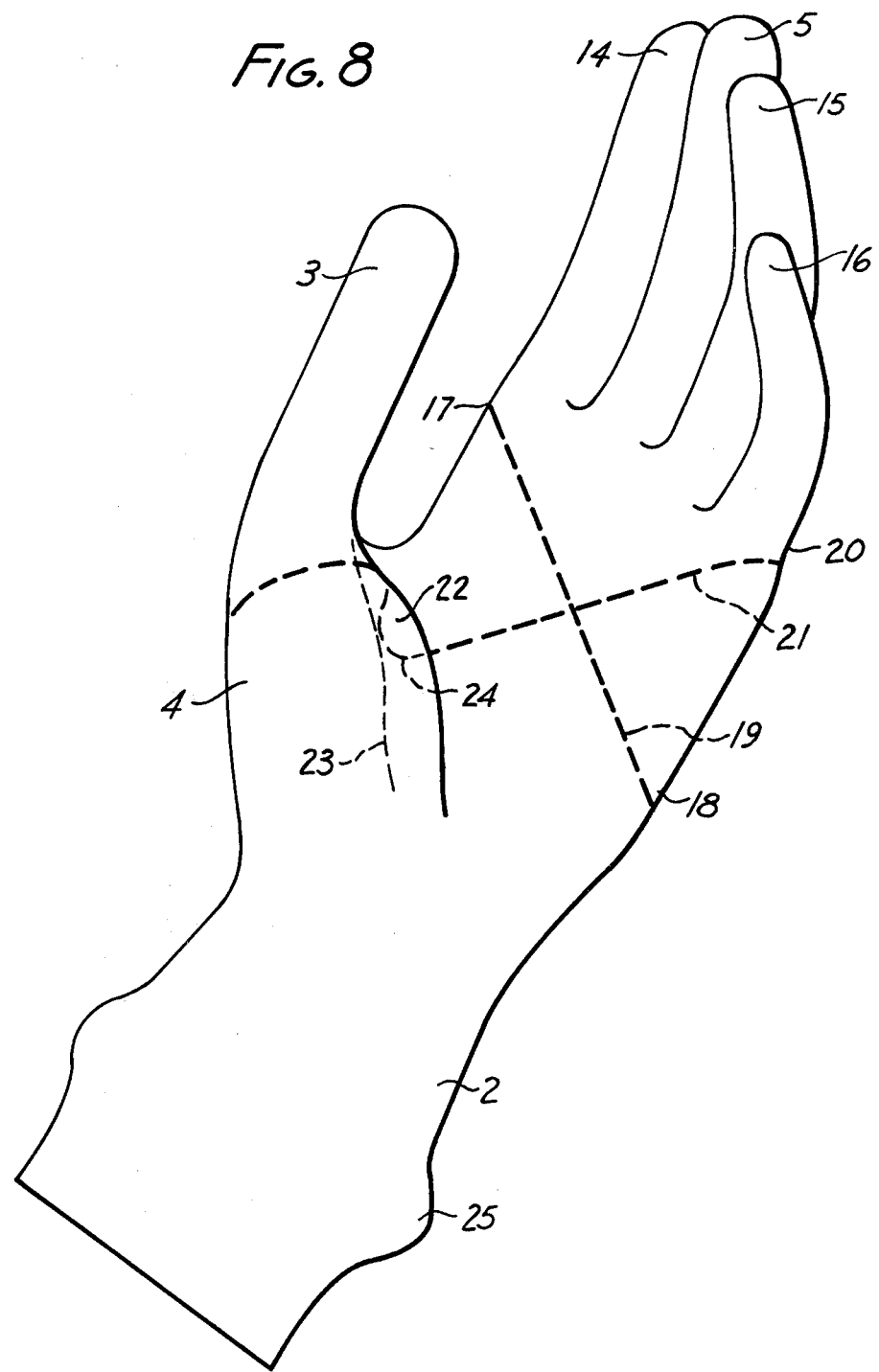
FIG. 8 is a prospective view showing the exaggerated undercut thumb ball section of the glove.

The surgeon's glove in FIG. 1 has a palm area 1, a cuff area 2, a thumb area 3, and a thumb ball area 4.

The glove has a series of fingers, such as 5, which have generally parallel sides 6 and 7 which provide for easy stripping of the glove from a mold. Preferably the distance 8 between the glove fingers is 0.200 to 0.300 inch to prevent webbing between the glove fingers during a latex dip forming operation.

The shape and configuration of the finger 5 section of the glove is best shown in FIGS. 2-6. While FIG. 2 shows a finger section of the glove, its relationship to the surgeon's fingernail when donned by such surgeon is shown by the phantom dotted fingernail positioned at 9. In the glove fingertip area at a location approximately midpoint of the wearer's fingernail is one of the most critical areas for tactile sensitivity in a surgeon's glove. It is this area which contacts the surgeon's thumb when the fingertip and thumbtip are brought together. The glove in the fingertip area designated at 10 is ovaled slightly from side to side of the glove finger. The glove also has a smaller cross-sectional area at this transverse oval section than at other portions of the glove finger.

Directly below sensitive tip section 10 is a first knuckle section 11, which is shown in FIG. 4 as being generally circular in cross-sectional shape. Thus, the first knuckle area can have approximately the same width as the glove fingertip area at 10 and thereby have sides that are parallel in both of these sections of the glove finger, but still provide more circumferential material at first knuckle 11 than at fingertip area 10.

Immediately behind first knuckle area 11 is a second knuckle area 12. This corresponds to the mid finger knuckle joint of the surgeon. The glove at second knuckle area 12 has a substantial oval in a direction from a front to back of the glove finger. This provides substantial circumferential material at the second knuckle to permit free flexing of this second knuckle of a surgeon's hand which is generally larger than his first knuckle. Immediately behind the second knuckle 12 is a finger base section 13 which is ovaled from front to back of the glove finger, but in a less pronounced oval than at second knuckle 12.

As can be seen by comparing FIGS. 3, 4, 5, and 6, the vertical distance in these four figures (representing width of glove finger) is substantially equal creating generally parallel sides for each glove finger to prevent webbing between the fingers and providing easy strip removal from a glove form. The variation and circumferential material in the glove finger area is varied throughout the finger by the varying dimensions being between a front and rear of the glove finger causing the differential ovaling as shown in FIGS. 3-6.

FIG. 7 shows the side elevational view of this glove in which the index finger 14, middle finger 5, ring finger 15, and little finger 16 become progressively more curved toward a front palm face of the glove. This configuration generally follows the natural contour of a surgeon's hand as he is preparing to grasp and manipulate surgical instruments.

In the propective view of FIG. 8, the improved palm and thumb ball area of the glove is shown. Because of the anatomy of the human hand, a glove is required to stretch only a small amount during hand manipulation in a diagonal direction from a base area 17 of the index finger to a heel area 18 of the palm. This stretch direction is shown by dotted line 19 on the glove.

Conversely, there is substantial stretch required in a diagonal direction across the glove palm from a ball of the thumb to a base 20 of little finger 16. This high degree of stretch required along diagonal 21 is because the thumb 3 and thumb ball 4 move inwardly as the thumb is brought in contact with the various fingers. To compensate for this high stretch requirement, and avoid a glove that is unduly tight along diagonal 21, the thumb ball portion 4 has been substantially exaggerated over the proportions of a human hand in an area 22. To illustrate this a dotted line 23 has been used to illustrate the approximate position of the thumb ball 23 of a human hand selected in size to approximate the size of the unstretched glove in FIG. 8. To provide additional material in the thumb ball, it is preferable to have an undercut section 24 indicated by the dots following the surface area of the glove. Thus, the surface configuration takes on an S-shape.

In the cuff area 2 of the glove, it is preferable to include corrugation, ribs, bulge, or other means to secure the cuff to a physician's gown. It is preferable that such securement means is in the area designated by 25 of FIG. 8.

FIG. 9 shows a first elevational view of the glove form 26 used to form the glove shown in FIG. 1. The general configuration of the glove form is identical to the glove in FIG. 1, and can be made of a porcelain material. Preferably there is a size indication means 27 on the glove form to form a bead or groove in the glove indicating its size. The glove form is longer than the intended glove, which has a cuff rear end at approximately 28 to provide a supporting structure on the glove form for the latex dipping machinery.

This glove is preferably made in a series of sizes as explained in co-pending application Ser. No. 846,928, filed Oct. 31, 1977, now U.S. Pat. No. 4,115,873, entitled Highly Stretchable Gloves and Method of Sizing Same. A related device for selecting glove sizes is described in co-pending application Ser. No. 846,924, filed Oct. 31, 1977, entitled Hand Meauring Device.

In the above description of the present invention, specific examples have been used to describe the invention. However, those skilled in the art will understand that certain modifications can be made to this example without departing from the spirit and scope of the invention.

I claim:

1. A highly stretchable glove, which has a front palm section, an offset thumb for fitting either a left or right hand, but not both, and a thumb ball section, wherein the improvement comprises: an exaggerated thumb ball section of the glove to provide added material in a direction diagonally across the glove palm from the thumb ball to a base of the glove's little finger and having a generally S-shaped profile along such diagonal with an undercut section adjacent such thumb ball, whereby the thumb can freely move toward and away from a glove finger without excessive stretching of the glove palm in this diagonal direction when the glove is stretchingly donned.

2. The glove as set forth in claim 1, wherein the exaggerated thumb ball portion of the glove has an S-shaped surface configuration in a diagonal direction from the thumb ball to a base of the glove's little finger.

3. A glove as set forth in claim 1, wherein the glove palm is proportionally equivalent to a human hand in a direction diagonally across the glove palm from a base of an index finger of the glove to a heel of the glove palm.

* * * * *